(12) United States Patent
Shahandeh et al.

(10) Patent No.: US 7,215,999 B1
(45) Date of Patent: May 8, 2007

(54) BATTERY CHARGE INDICATOR FOR IMPLANTABLE PACEMAKERS AND DEFIBRILLATORS

(75) Inventors: Reza Shahandeh, Thousand Oaks, CA (US); George I. Isaac, Port Hueneme, CA (US)

(73) Assignee: Pacesetter, Inc., Sylmar, CA (US)

( * ) Notice: Subject to any disclaimer, the term of this patent is extended or adjusted under 35 U.S.C. 154(b) by 470 days.

(21) Appl. No.: 10/636,724

(22) Filed: Aug. 6, 2003

(51) Int. Cl.
*A61N 1/00* (2006.01)

(52) U.S. Cl. .......................... 607/29; 607/27

(58) Field of Classification Search ............ 607/27–29
See application file for complete search history.

(56) References Cited

U.S. PATENT DOCUMENTS

| | | | |
|---|---|---|---|
| 4,259,639 A | 3/1981 | Renirie | 324/430 |
| 4,556,061 A * | 12/1985 | Barreras et al. | 607/32 |
| 4,686,988 A | 8/1987 | Sholder | 128/419 PT |
| 4,707,795 A * | 11/1987 | Alber et al. | 702/63 |
| 4,708,142 A | 11/1987 | DeCote, Jr. | 128/419 PT |
| 4,712,555 A | 12/1987 | Thornander et al. | 128/419 PT |
| 4,715,381 A * | 12/1987 | Moberg | 607/29 |
| 4,729,376 A | 3/1988 | DeCote, Jr. | 128/419 PT |
| 4,766,902 A * | 8/1988 | Schroeppel | 607/9 |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PT |
| 4,944,299 A | 7/1990 | Silvian | 128/419 PG |
| 5,350,410 A | 9/1994 | Kleks et al. | 607/28 |
| 5,458,624 A | 10/1995 | Renirie et al. | 607/29 |
| 6,148,235 A | 11/2000 | Kuiper | 607/29 |
| 6,167,309 A | 12/2000 | Lyden | 607/29 |
| 6,275,734 B1 | 8/2001 | McClure et al. | 607/27 |
| 6,400,988 B1 | 6/2002 | Gurewitsch | 607/29 |
| 2001/0034541 A1 | 10/2001 | Lyden | 607/29 |

FOREIGN PATENT DOCUMENTS

WO WO 99/14612 3/1999

* cited by examiner

*Primary Examiner*—George R. Evanisko
*Assistant Examiner*—Michael Kahelin

(57) ABSTRACT

Current usage from a battery in an implantable cardiac device is tracked. The apparatus includes a battery current sensor having multiple current ranges. The current sensor produces a first signal representative of current drawn from a battery. A current range selector selects a current range for the battery current sensor and produces a second signal representative of the current range. An accumulator accumulates the first signal based on the second signal over time to generate an output signal representing usage of the battery.

13 Claims, 6 Drawing Sheets

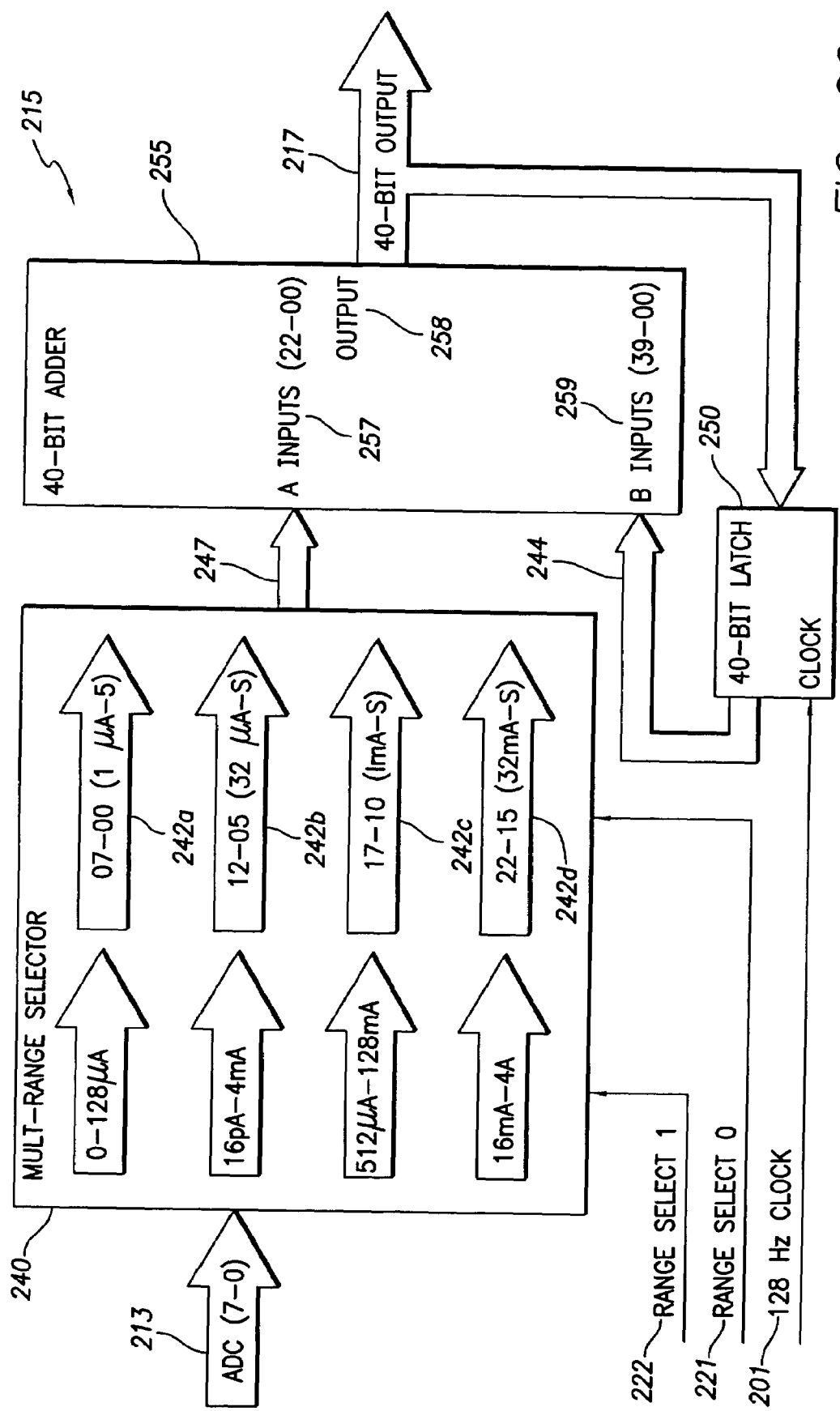

BATTERY CHARGE INDICATOR FOR IMPLANTABLE PACEMAKERS AND DEFIBRILLATORS

FIELD OF THE INVENTION

The present invention relates generally to implantable cardiac devices and, more particularly, to keeping track of battery usage in implantable cardiac devices

BACKGROUND

An implantable cardiac device is a medical device that is implanted in a patient to monitor electrical activity of the heart and to deliver appropriate electrical and/or drug therapy, as required. Implantable cardiac devices include, for example, pacemakers, cardioverters and defibrillators. The term "implantable cardioverter defibrillator" or simply "ICD" is used herein to refer to any implantable cardiac device.

An ICD employs a battery to power its internal circuitry and to generate electrical therapy. The electrical therapy can include, for example, pacing pulses, cardioverting pulses and/or defibrillator pulses.

When a battery is manufactured, its energy capacity is known. Specifically, it is known how many Ampere-Hours of energy the battery can deliver. Based on the known battery energy capacity and based on predicted usage, battery life can be predicted and a replacement interval established. With this approach, a conservative margin in remaining battery life is observed to prevent device failure due to a depleted battery. Alternatively, actual battery usage can be tracked, and the device can be replaced when the actual remaining energy capacity of the battery falls below a predetermined threshold. This second approach of tracking battery usage and replacing a device when replacement is actually required is preferred since it reduces unnecessary device replacements. It could, also, be used to inform the physician of unexpected battery depletion or excessive current drain that might be a sign of malfunction.

Conventional methods for tracking battery usage use estimation techniques to determine how much energy is left in the battery. As previously mentioned, the estimation techniques are not accurate and require observation of conservative margins. Other conventional systems measure battery voltage and use the voltage measurement as an indicator of how much energy is left in the battery. This method is problematic because of unexpected drops and hikes in voltage within the battery circuit which can lead to inaccurate battery life predictions.

What is needed is a better and more accurate system and method for keeping track of the battery usage, so that the end-of-life of the battery can be predicted with greater precision.

SUMMARY

The present invention includes a method and apparatus for tracking current usage over time from a battery in an implantable cardiac device. The apparatus includes a battery current sensor having multiple current ranges. The current sensor produces a first signal representative of current drawn from a battery. A current range selector selects a current range for the battery current sensor and produces a second signal representative of the current range. An accumulator accumulates over time the first signal based on the second signal to generate an output signal representing usage of the battery.

In a preferred embodiment, the current sensor and current range selector together form an automatic, multi-range current sensor. Current is sensed as a voltage across a resistance placed in series with the load current being drawn from the battery. A higher resistance is used with low currents and a lower resistance is used with higher currents. This yields a current sensor with good sensitivity and accuracy across a wide current range while keeping parasitic power loss to a minimum.

The multi-range current sensor classifies the drawn current into a selected one of four ranges. For example, a first current range is up to about 128 μAmps, a second current range is up to about 4 mAmps, a third current range is up to about 128 mA, and a fourth current range is up to about 4 Amps. The range is selected by the current sensor as follows.

As indicated above, the current is sensed as a voltage across a resistance. An amplifier amplifies the voltage. A window comparator compares the magnitude of the voltage to two reference voltages. Based on this comparison, the comparator produces up or down signals to a counter, causing the counter to increment or decrement. The output of the counter represents a range select signal. A decoder produces a range code from the range select signal. The current sensor uses the range code to select the resistance value placed in series with the battery load current. The range select signal is then used by the accumulator as an indication of the range of the current measured.

The amplified voltage representing the load current is provided to an analog to digital converter and converted to a digital value. The digital value, representing the load current, is then provided to the accumulator. The accumulator uses the range select signal to determine the weight to be given to the digital value representing the load current. In a preferred embodiment, the digital value representing the load current is an 8-bit number. The accumulator is a 40-bit accumulator. Weighting of the digital value is done by selecting where in the 40-bits, the 8-bit value is added. For example, for high current values, the range select signal will cause the accumulator to add the 8-bit value into more significant bits of the accumulator (e.g., bits 22 through 15, with bit 39 being the most significant bit in the accumulator). For low current values, the range select signal will cause the accumulator to add the 8-bit value into less significant bits of the accumulator (e.g., bits 7 through 0, with bit 0 being the least significant bit in the accumulator).

The method of the invention involves tracking battery usage in an implantable cardiac device. The method includes the steps of: (1) sensing a current being drawn from the battery, (2) generating a first signal representing the current; (3) classifying the current into a selected one of a plurality of predetermined ranges; (4) generating a second signal indicative of the selected range; (5) using the second signal to accumulate the first signal over time; and (6) generating, based on the accumulation, a third signal representing usage of the battery. The generating step includes: producing a voltage signal representing the current, amplifying the voltage signal, and digitizing the voltage signal to generate the first signal.

In a preferred embodiment, the classifying step includes classifying the current into a selected one of four predetermined ranges: a first current range of up to about 128 μAmps, a second current range of up to about 4 mAmps, a third current range of up to about 128 mA, and a fourth current range of up to about 4 Amps.

The accumulation includes weighting the digitized voltage signal based on the second signal and accumulating the digitized voltage signal over time based on a clock signal.

Further features and advantages of the present invention as well as the structure and operation of various embodiments of the present invention are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements. Additionally, the leftmost digit of a reference number identifies the drawing in which the reference number first appears.

FIG. 2C is a block diagram of a multi-range digital accumulator circuit, as shown in FIG. 2A, according to the present invention.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Figure 1A:
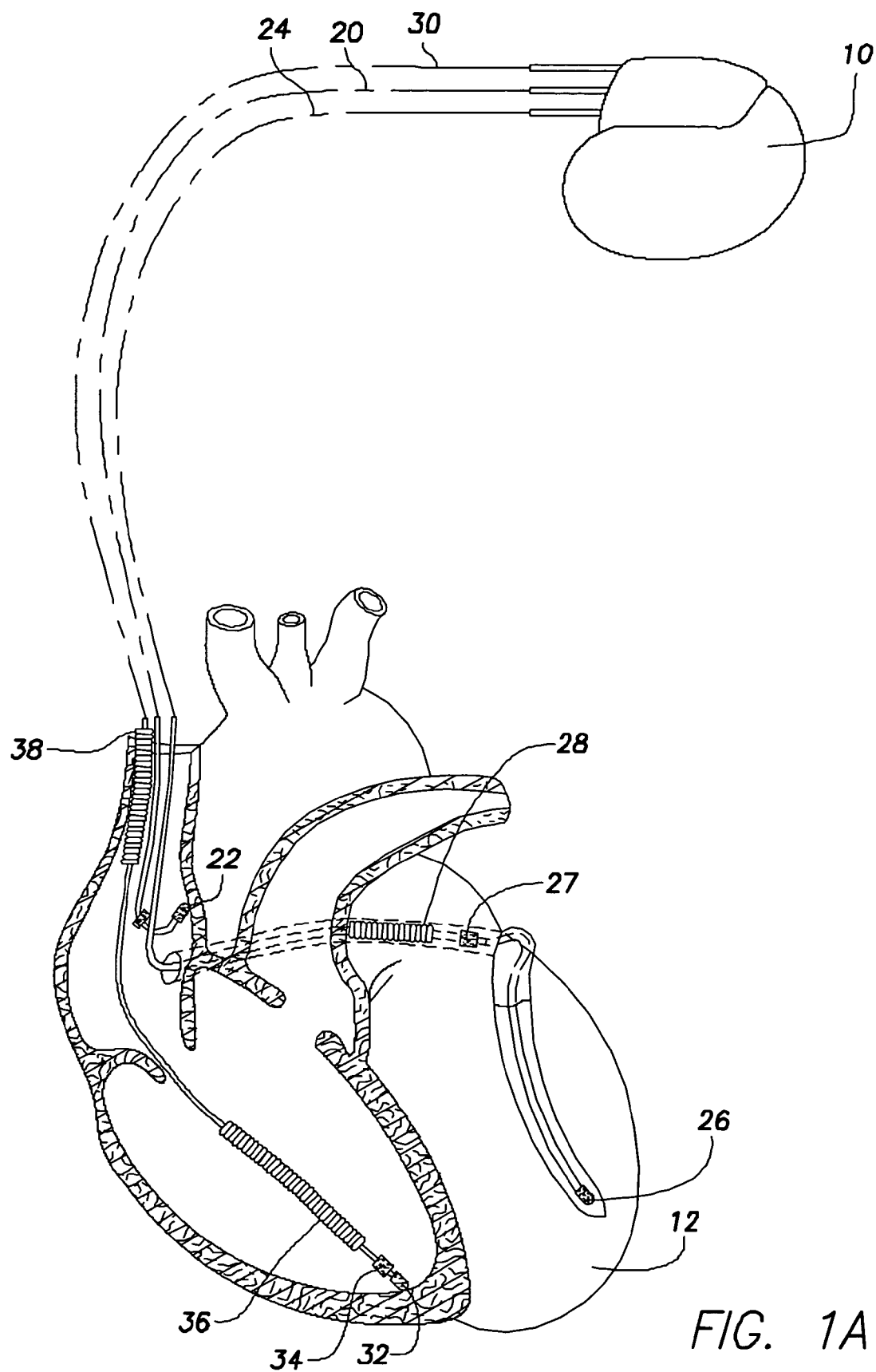
FIG. 1A is a simplified diagram illustrating an ICD in electrical communication with at least three leads implanted into a patient's heart for delivering multi-chamber stimulation and shock therapy.
Figure 1B:
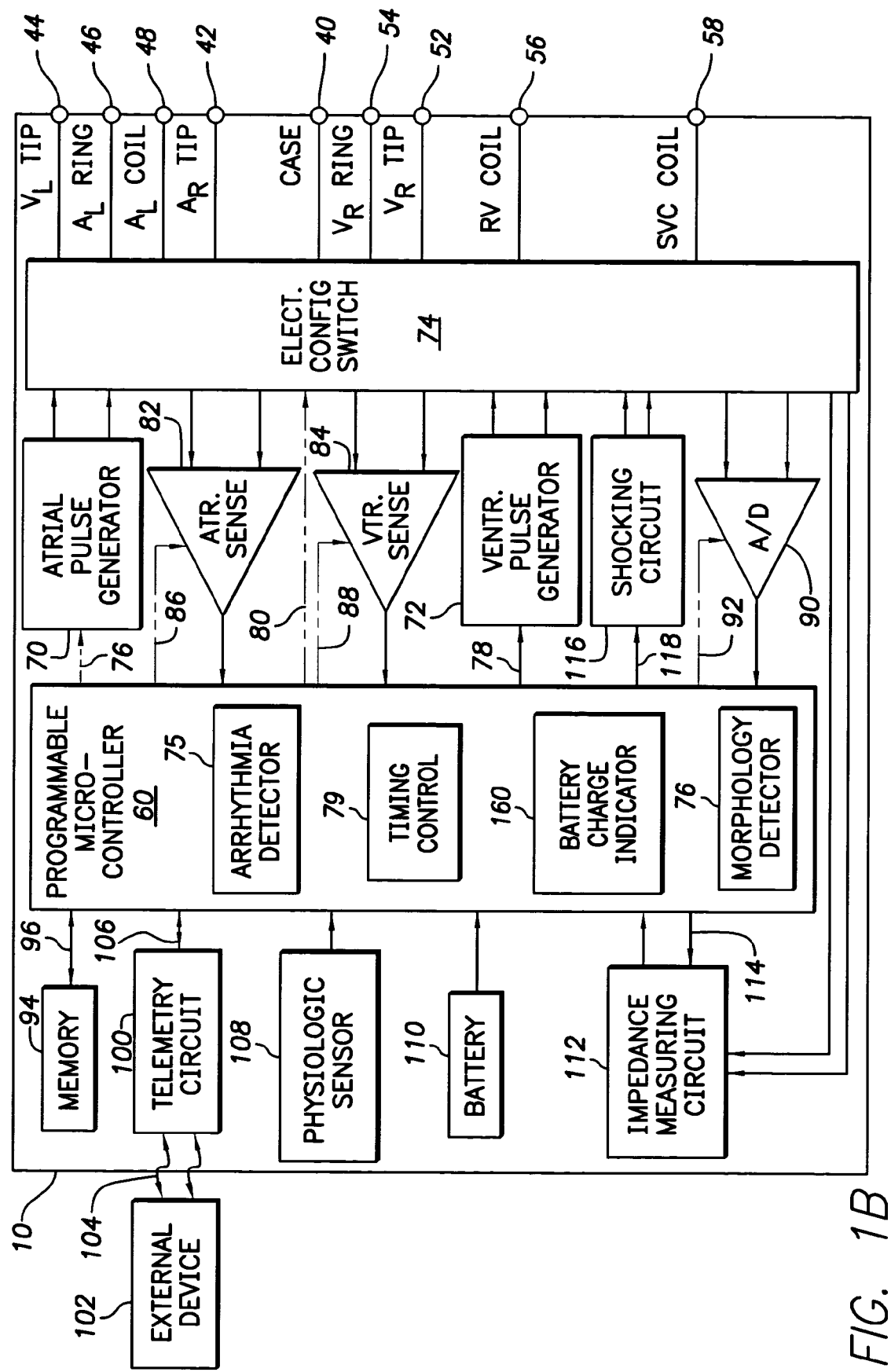
FIG. 1B is a functional block diagram of an ICD which can provide cardioversion, defibrillation and pacing stimulation in four chambers of a heart.

Before describing the invention in detail, it is helpful to describe an example environment in which the invention may be implemented. The present invention is particularly useful in the environment of an implantable cardiac device. Implantable cardiac devices include, for example, pacemakers, cardioverters and defibrillators. The term "implantable cardioverter defibrillator" or simply "ICD" is used herein to refer to any implantable cardiac device or implantable cardioverter defibrillator ("ICD"). FIGS. 1A and 1B illustrate such an environment.

As shown in FIG. 1A, there is an exemplary ICD 10 in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

FIG. 1B shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 1B, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art. In specific embodiment of the present invention, microcontroller 60 performs some or all of the steps associated with tracking battery usage in accordance with the present invention.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the ICD's and their inter-relationship, see U.S. Pat. No. 4,788,980 (Mann et al.). The '052, '555, '298 and '980 patents are incorporated herein by reference.

As shown in FIG. 1B, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70,72, may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A—A) delay, ventricular interconduction (V—V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In the preferred embodiment, ICD 10 further includes a physiologic sensor 108, that can be used to detect changes in cardiac performance or changes in the physiological condition of the heart. Accordingly, microcontroller 60 can respond by adjusting the various pacing parameters (such as rate, AV Delay, RV-LV Delay, V—V Delay, etc.) in accordance with the embodiments of the present invention. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 additionally includes a battery 110 which provides operating power to all of the circuits shown in FIG. 1B. For ICD 10, which employs shocking therapy, battery 110 must be capable of operating at low current drains for long periods of time, and then be capable of providing high-current pulses (for capacitor charging) when the patient requires a shock pulse. Battery 110 must also have a predictable discharge characteristic so that elective replacement time can be detected. Accordingly, ICD 10 preferably employs lithium/silver vanadium oxide batteries, as is true for most (if not all) current devices.

ICD 10 further includes a magnet detection circuitry (not shown), coupled to microcontroller 60. It is the purpose of the magnet detection circuitry to detect when a magnet is placed over ICD 10, which magnet may be used by a clinician to perform various test functions of ICD 10 and/or to signal microcontroller 60 that the external programmer 102 is in place to receive or transmit data to microcontroller 60 through telemetry circuit 100.

As further shown in FIG. 1B, ICD 10 is shown as having an impedance measuring circuit 112 which is enabled by microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

In accordance with the present invention, ICD 10 further includes a battery charge indicator circuit 160. Battery charge indicator circuit 160 monitors current drawn from battery 110 to improve prediction of when battery 110 needs replacement. Battery charge indicator circuit 160 is further described in FIGS. 2A–2C below. Also, FIG. 3 further illustrates a method for tracking battery current usage in ICD 10.

Consumption of current in ICD 10 happens in various current ranges depending on the mode of operation. For example, in one embodiment, ICD 10 can draw current anywhere in the range of 10 μA to 4 A. ICD 10 can be drawing 3–4 A over a short period of time (e.g., to charge the high voltage capacitors) and 10–20 μA over a long period of time (e.g., during monitoring when no electrical stimuli are being delivered). The present invention is able to accommodate tracking of different current usage from the battery during these different modes of operation.

The battery current consumption is normally in the μA range for pacemakers with peaks occurring during the generation of the pacing pulses. For a cardioverter or defibrillator, the high voltage capacitor charging uses battery current that is typically in the range of about 3 A, and other functions of the battery circuit may draw 10 mA or more from the battery. The battery charge indicator circuit of the present invention is able to integrate all these different currents over the lifetime of the battery to accurately keep track of actual charge (i.e., current multiplied by time or Ampere seconds (A-S)) drawn from the battery. Because the low current drains occur over much longer periods of time than the higher current drains, the low current drains typically account for a significant portion of the battery consumption.

Figure 2A:
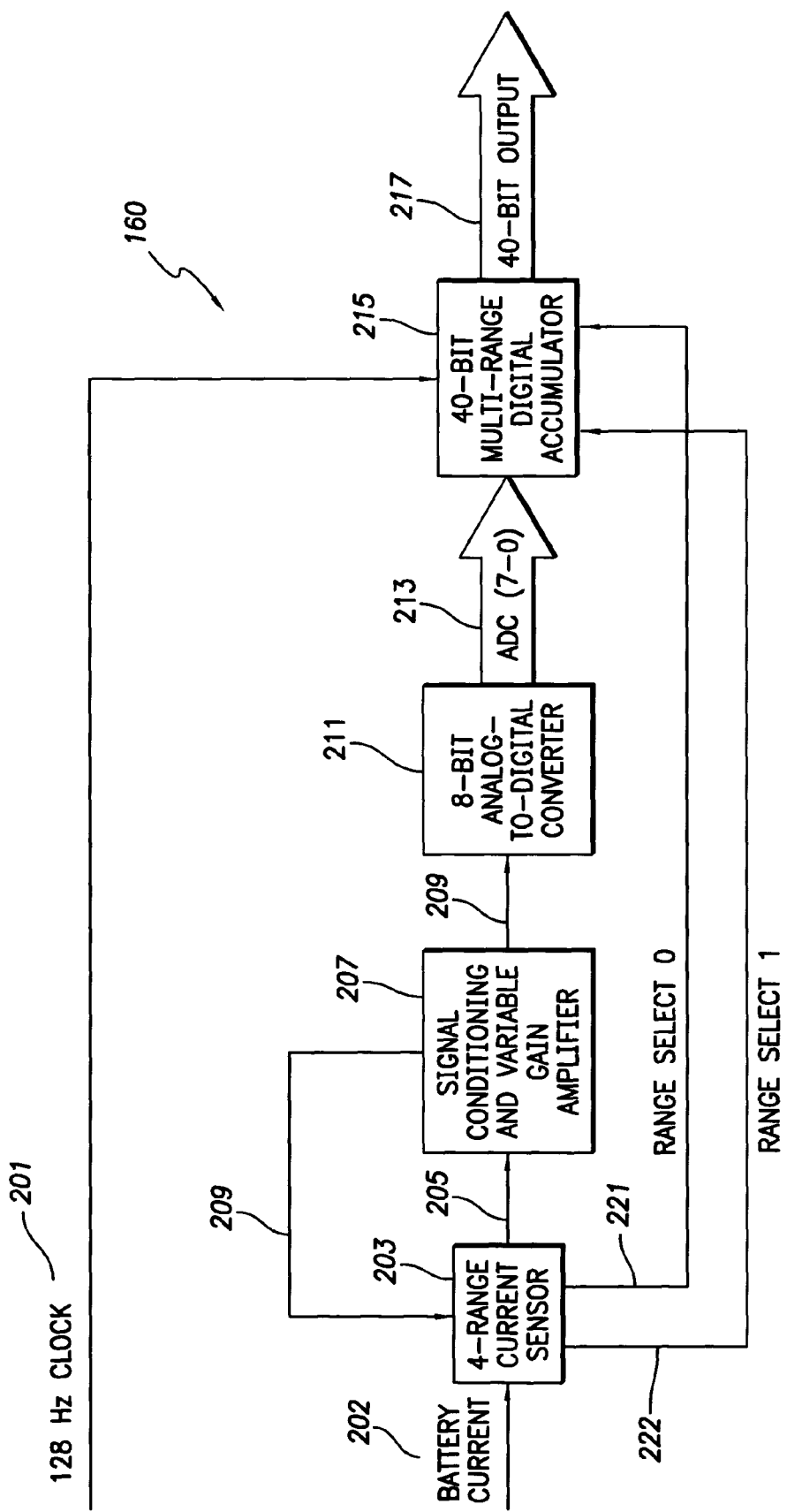
FIG. 2A is a block diagram of a battery charge indicator circuit, according to the present invention.

FIG. 2A is a block diagram of battery charge indicator circuit 160 according to the present invention. Battery charge indicator circuit 160 includes a multirange current sensor 203, a signal conditioning and variable gain amplifier (VGA) 207, an analog to digital converter (ADC) 211 and a multi-range digital accumulator 215. A load current 202 is passed from battery 110 through multirange current sensor 203. Multirange current sensor 203 produces a voltage signal 205 representative of the magnitude of load current 202. Multirange current sensor 203 also produces range select signals 221, 222 representing a range of the load current. Range select signals 221, 222 are provided to accumulator 215.

VGA 207, together with the multirange current sensor 203, conditions and amplifies voltage signal 205 to be within an operating range of ADC 211. Voltage signal 205 becomes an amplified signal 209 that is digitized by ADC 211. In this embodiment of the present invention, ADC 211 digitizes amplified signal 209 into an 8-bit digital signal 213. Bits of digital signals 213 are then accumulated by accumulator 215. In one embodiment, ADC 211 samples the signal 209, 128 times per second, i.e. it generates an 8-bit output about every 7.8 ms.

Accumulator 215 generates an output signal 217 representing the amount of energy that has been drawn from battery 110. Output signal 217 is received by microcontroller 60 (not shown in FIG. 2A). In this embodiment, the capacity of accumulator 215 is forty bits, therefore, output signal 217 is a forty-bit output signal. Practically, the microcontroller 60 may utilize, for example, only the most significant 8 or 16 bits.

Because ICD 10 draws various currents from battery 110, load current 202 fluctuates between several different "current ranges." Each current range corresponds to a specific charge amount or energy range that is being drawn from the battery 110. In this embodiment of the present invention, battery charge indicator circuit 160 is configured to operate in four "current ranges." In other words, based on different magnitudes of load current 202, multirange current sensor 203 generates different voltage signals 205 that correspond to different current ranges. Because the voltage signal 205 is amplified and digitized, a lower load current 202 generates a digital signal 213 corresponding to a lower "current range" and, thus, lower charge consumption from battery 110. Conversely, a higher load current 202 generates a digital signal 213 corresponding to a higher "current range" and, thus, higher charge consumption from battery 110.

Figure 2B:
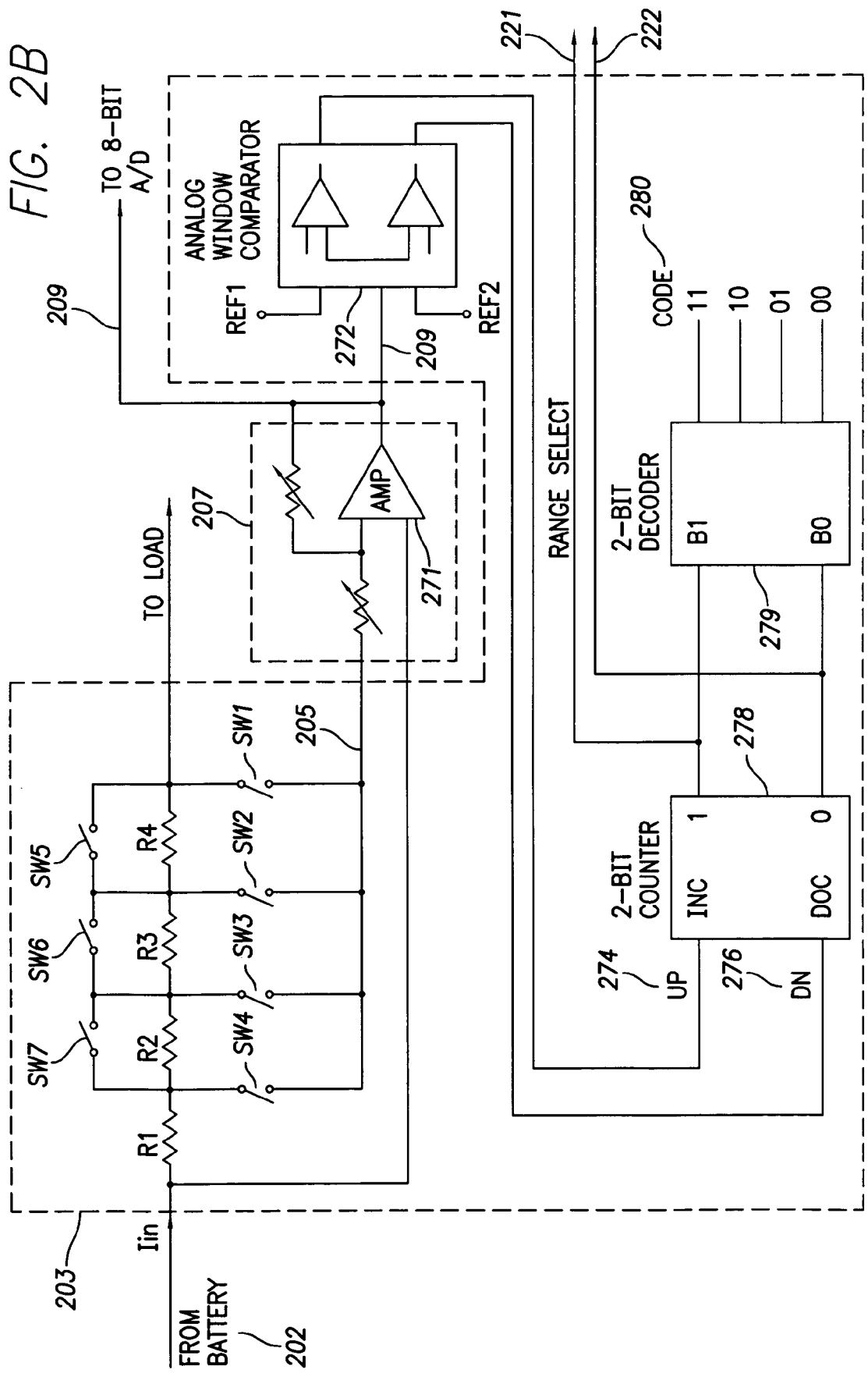
FIG. 2B is a circuit diagram of a multirange current sensor within the battery charge indicator circuit shown in FIG. 2A, according to the present invention.

FIG. 2B is a circuit diagram showing multirange current sensor 203 and VGA 207. Multirange current sensor 203 includes resistors R1, R2, R3, and R4 connected in series with load current 202. Switches SW1–SW7 are coupled to resistors R1–R4. Switches SW1–SW7, in various configurations (i.e., some switches closed and some open), route the current drawn from battery 110 through various series combinations of resistors R1–R4. Switches SW1–SW7 are controlled through various logic operations described below. As would be understood by one having ordinary skill in the art, other combinations of switches and resistors are possible.

Load current passing through various combinations of resistors R1–R4, will produce a voltage drop that is measured across the resistors. This voltage drop is then measured as an indication of load current 202. Different resistances are chosen based on the magnitude of the current. For example, smaller resistances are placed in series with larger currents, and larger resistances are placed in series with smaller currents, so that the measured voltage drop can be controlled to be within a desired voltage range.

As described above, ICD 10 consumes energy in predetermined current ranges depending on its mode of operation. Each current range corresponds to a particular resistor (e.g., R1) or combination of resistors (e.g., R1–R4) being selected for load current 202 to pass through. This embodiment of the present invention has four current ranges. For example, ICD 10 can consume energy from battery 110 in a first current range of up to about 128 μA, a second current range of up to about 4 mA, a third current range of up to about 128 mA, or a fourth current range of up to about 4 A. The following Table 1 illustrates a relationship between each "current range" and corresponding resistors R1–R4 being connected in series with load current 202.

TABLE 1

Relationship between "current ranges" and activation of R1–R4

| Current Range | Digital Code | Resistors being connected to load current 202 | Current Range |
| --- | --- | --- | --- |
| 1 | 00 | R1 & R2 & R3 & R4 | ~128 μA |
| 2 | 01 | R1 & R2 & R3 | ~4 mA |
| 3 | 10 | R1 & R2 | ~128 mA |
| 4 | 11 | R1 | ~4 A |

In Table 1, the "current range" column indicates in which current range ICD 10 is drawing current from battery 110. The "digital code" column indicates a digital code related to each current range. The digital code is discussed in detail below. The "resistors being connected to load current 202" column indicates resistors or combination of resistors R1–R4 connected in series with load current 202. The "current" column indicates a current range within which ICD 10 is drawing current. For example, the second current range corresponds to resistors R1, R2, and R3 being connected in series with load current 202, and ICD 10 drawing current in the range of up to 4 mA.

Resistors or combinations of resistors R1–R4 are connected in series with load current 202 using switches SW1–SW7. The following Table 2 illustrates which switches or combinations of switches SW1–SW7 activate corresponding resistors or groups of resistors R1–R4. The digital code, shown in Table 1, indicates a switch being closed, along with appropriate resistors R1–R4 being connected to load current 202.

TABLE 2

Resistor activation and corresponding switching scheme

| Switch | SW1 | SW2 | SW3 | SW4 | SW5 | SW6 | SW7 |
|---|---|---|---|---|---|---|---|
| Code for which switch is closed | 00 | 01 | 10 | 11 | 01 + 10 + 11 | 10 + 11 | 11 | where "+" denotes logical "OR".

Digital code 00 indicates that switch SW1 is closed, and switches SW2–SW7 are open. Since SW1 is closed, load current 202 flows through resistors R1, R2, R3, and R4, as shown in FIG. 2B and Table 1. This means that ICD 10 is drawing current from battery 110 in a first current range of up to about 128 µA.

Digital code 01 indicates that switches SW2 and SW5 are closed. As a result, load current 202 flows through resistors R1, R2 and R3. Resistor R4 is bypassed. This means that ICD 10 is drawing current from battery 110 in a second current range of up to about 4 mA.

Digital code 10 indicates that switches SW3, SW5 and SW6 are closed. As a result, load current 202 flows through resistors R1 and R2. Resistors R3 and R4 are bypassed. This means that ICD 10 is drawing current from battery 110 in a third current range of up to about 128 mA.

Digital code 11 indicates that switches SW4, SW5, SW6 and SW7 are closed. As a result, load current 202 flows through resistor R1. Resistors R2, R3 and R4 are bypassed. This means that ICD 10 is drawing current from battery 110 in a fourth current range of up to about 4 A.

The digital codes control logic circuitry, within multirange current sensor 203, that controls the configuration of switches SW1–SW7. The digital codes are generated as discussed below.

As shown in FIG. 2B, VGA 207 includes an operational amplifier 271 which receives voltage signal 205 (representing the voltage drop across the selected combination of resistors R1–R4) from. Amplifier 271 amplifies voltage signal 205 to produce amplified signal 209. As depicted in FIGS. 2A and 2B, amplified signal 209 is provided by analog-to-digital converter 211 for conversion to a digital signal, and then to accumulator 215 for accumulation. Amplified signal 209 is also provided back to multirange current sensor 203 for range selection.

Referring to FIG. 2B, multirange current sensor 203 further includes an analog window comparator 272, a two-bit counter 278 and a two-bit decoder 279. Analog window comparator 272 is coupled to receive the output of amplifier 271 and to generate an UP signal 274 or a DOWN signal 276. Two-bit counter 278 is coupled to receive UP signal 274 and DOWN signal 276 from comparator 272 and produces a two-bit count value that is supplied to two-bit decoder 279. The two-bit count value also serves as range select signals 221, 222. The output of two-bit decoder 279 is a two-bit code value 280.

Comparator 272 compares voltage signal 205 to threshold voltages REF1 and REF2, REF1 being higher than REF2. Threshold voltages REF1 and REF2 are set such that REF1/REF2 is greater than the non-overlapping ratio which, in the current invention, is 32 or 5 bits. This provides Hysteresis when switching ranges and prevent system oscillation. Threshold voltages REF1 and REF2 define a voltage window. Based on this comparison, analog window comparator 272 generates either UP signal 274 or DOWN signal 276. UP signal 274 and DOWN signal 276 indicate, respectively, whether voltage signal 209 is greater than or less than respective threshold voltages REF1 and REF2.

Normally, in any current range, the voltage signal 209 is between threshold voltages REF1 and REF2 (i.e., the voltage signal is within the window), then both UP signal 274 and DOWN signal 276 will be a logical LOW. This will cause counter 278 to maintain its value without counting. As a result, the range select signals and range code will not change.

If voltage signal 209 is greater than threshold voltage REF1, then UP signal 274 will be a logical HIGH, and DOWN signal 276 will be a logical LOW. This will cause counter 278 to count up. Counting up increases the range select signals 221, 222 and the range code 280. Since, the range code controls range selection by multirange current sensor 203, a different current range is selected by reconfiguring switches SW1–SW7. In this example, increasing range code 280 will cause the resistance placed in the path of the load current to be reduced to thereby reduce voltage signal 205.

Conversely, if voltage signal 209 is less than REF2, then DOWN signal 276 will be a logical HIGH, and UP signal 274 will be a logical LOW. This will cause counter 278 to count down. Counting down decreases the range select signals 221, 222 and the range code 280 and results in the resistance placed in the path of the load current to be increased to thereby increase voltage signal 205.

The following Table 3 illustrates various comparisons between voltage signal 209 and threshold voltages REF1 and REF2.

TABLE 3

Comparison between voltage signal 209 and threshold voltages REF1 and REF2

| Condition | UP signal 274 | DOWN signal 276 |
|---|---|---|
| voltage signal 209 > REF1 | HIGH | LOW |
| voltage signal 209 between REF1 and REF2 | LOW | LOW |
| voltage signal 209 < REF2 | LOW | HIGH |

Table 4 illustrates how range select signals 221 and 222 correspond to digital codes 280.

TABLE 4

Correlation between range select signals 221, 222 and digital codes 280

| Digital Code 280 | Range select signal 221 | Range select signal 222 |
|---|---|---|
| 11 | 1 | 1 |
| 10 | 1 | 0 |
| 01 | 0 | 1 |
| 00 | 0 | 0 |

As previously discussed, range select signals 221 and 222 indicate from which current range, ICD 10 is drawing current from battery 110. Range select signals 221 and 222 are supplied to accumulator 215. Range codes 280 are used only internal to multirange current sensor 203 for range selection.

Because load current 202 is continuously supplied to multirange current sensor 203, voltage signal 209 is continuously compared to threshold voltages REF1 and REF2. Therefore, digital codes 280, controlling switches SW1–SW7, are continuously generated as necessary causing resistors or combination of resistors R1–R4 to be switched in and out of series connection with load current 202, as necessary. Overlap between the current ranges provides some hysteresis to prevent system oscillation between current ranges. This overlap also reduces the importance of the accuracy of the window comparator that causes range selection when a current is near a range boundary.

In an example embodiment, resistor R1 has a value of 16 mΩ (0.016Ω), resistor, R2 has a value of 0.5Ω, resistor R3 has a value of 16Ω, and resistor R4 has a value of 500Ω. Given the maximum current that will be passed through each resistor (or resistor combination), these resistances will result in a maximum voltage of about 64 mV (voltage signal 205). In addition, amplifier 207 will have a gain of about 40 to yield an output voltage of about 2.5 V maximum at the input of window comparator 272 (voltage signal 209). In this embodiment, REF1 is set at about 2.1 V, and REF2 is set at about 50 mV.

Based on these example values, the thresholds at which multirange current sensor 203 will change range are set forth below in Table 5.

TABLE 5

Example Current Range Parameters

| Range | Resist. | LSB | Lower Threshold | Upper Threshold |
|---|---|---|---|---|
| 1 | 516.5 Ω | 0.5 μA | — | 102 μA |
| 2 | 16.5 Ω | 16 μA | 75.8 μA | 3.2 mA |
| 3 | 0.5 Ω | 0.5 mA | 2.5 mA | 105 mA |
| 4 | 0.016 Ω | 15.6 mA | 78.1 mA | — |

Note that Table 5 corresponds to Table 1 set forth above. The resistance values listed are total resistances calculated using the resistor values set forth in the example embodiment discussed immediately above. The least significant bit (LSB) values are calculated by dividing the current range value by 256 (since 8 bits are used to represent the current). The lower threshold value is calculated by dividing the lower threshold voltage (e.g., 0.05V) by the product of the gain (e.g., 40) of amplifier 207 and the total resistance. For example, for current range 2, the equation is 0.05V/(40·16.5Ω)=75.8 μA. The upper threshold value is calculated by dividing the upper threshold voltage (e.g., 2.1V) by the product of the gain (e.g., 40) of amplifier 207 and the total resistance. For example, for current range 2, the equation is 2.1V/(40·16.5Ω)=3.2 mA.

As illustrated by Table 5, overlap between the current ranges provides some hysteresis. For example, multirange current sensor 203 will switch from range 1 to range 2, when the current reaches 102 μA but will not switch back from range 2 to range 1 until the current falls below 75.8 μA.

Referring again to FIG. 2A, ADC 211 receives amplified voltage signal 209 and digitizes it. Amplified voltage signal 209 is converted into an 8-bit digital signal 213. Digital signal 213 is then supplied to accumulator 215. Digital signal 213, along with range select signals 221 and 222, identifies a particular current value. The bits representing digital signal 213 are accumulated by accumulator 215 as described below.

In the preceding example and throughout the text, all values and ranges are provided as examples to illustrate the invention and selection of appropriate components. For example, since ranges 2, 3 and 4 cover exclusively the most significant five bits of the respective range, the exact value of each of these ranges is 32 times the preceding range. In this embodiment, Range 1 is chosen to be 128 uA. Accordingly, Range 2 should be 4.096 mA, and Range 3 would be 131.072 mA and so on. The same is true for the resistor values that determine each range. In FIG. 2B, R1 (which is the Range 4 sense resistor) is chosen to be 0.016 Ohm. Consequently, the Range 3 sense resistor (which is R1+R2), according to Table 1, makes R2 equal to 32*0.016−0.016=0.496 Ohm. Values of the other sense resistors can be calculated in the same manner. It would be apparent to a person skilled in the art to choose, for example, a value for the Range 1 sense resistor and then calculate values for the other sense resisters accordingly. Similarly, a value for current Range 4 may be arbitrarily selected and values for the other ranges selected accordingly. Other alternatives could also be implemented, e.g., number of ranges, number of overlap bits and/or number of resolution bits.

FIG. 2C is a block diagram illustrating accumulator 215, according to the present invention. Accumulator 215 includes a multi-range selector 240, a forty-bit adder 255 and a forty-bit latch 250 clocked by a clock signal 201. Multi-range selector 240 receives digital signal 213 from ADC 211. Multi-range selector 240 processes digital signal 213 based on range select signals 221 and 222. As described above, range select signals 221 and 222 indicate the current range of digital signal 213. Multi-range selector 240 includes digital bit ranges 242a–242d which correspond to current ranges one through four as set forth in Table 1 above. The following Table 6 illustrates digital bit ranges 242 and corresponding current ranges.

TABLE 6

Digital bit ranges and corresponding current ranges.

| Current Range | Digital bit range |
|---|---|
| ~128 μA | bits 07–00 |
| ~4 mA | bits 12–05 |
| ~128 mA | bits 17–10 |
| ~4 A | bits 22–15 |

Because, in this embodiment of the present invention, accumulator 215 is a forty-bit accumulator, each digital bit range 242 corresponds to a certain number of bits (e.g., 8 bits in this embodiment, because digital signal 213 is an 8-bit value). Table 6 illustrates which bit positions correspond to which current range. For example, the first current range is represented by bit positions 07–00, the second current range is represented by bit positions 12–05, the third current range is represented by bit positions 17–10, and the fourth current range is represented by bit positions 22–15. The remaining bits of the accumulator are used for overflow as current values are accumulated.

When multi-range selector 240 receives digital signal 213 from ADC 211, it selects a particular digital bit range 242 based on range select signals 221,222. For example, if multi-range selector 240 receives range select signals 221, 222 of "11," digital signal 213 is indicated as corresponding to bit range 242d (bit positions 22–15). In response to this range select signal, multi-range selector 240 will produce a 23-bit word with the 8-bit current value shifted into the appropriate bit positions.

The 23-bit word produced by multi-range selector 240 is passed on line 247 to adder 255 at input 257. Adder 255 adds this 23-bit word to the current accumulated value 249 received at input 259 from 40-bit latch 250. Adder 255 then outputs the sum value 217 representing an accumulation of all current drawn from battery 110 over time. This sum value 217 is also stored in 40-bit latch 250. In this manner, adder 255 and latch 250 accumulate load current values received from selector 240. Prior to receipt by adder 255, each current value received from selector 240 has been shifted to the appropriate significant bit position as indicated by range select signals 221,222 prior to receipt by adder 255.

Latch 250 is clocked by a 128 Hz clock signal 201. This clock signal controls the accumulation rate of accumulator 215.

The accumulated current value 217 is provided to microcontroller 60 and is used determine battery usage. In the embodiment depicted in FIG. 1B, battery charge indicator 160 is depicted as being part of microcontroller 60. In an alternate embodiment, battery charge indicator 160 is implemented with circuitry within ICD 10, but distinct from microcontroller 60.

The following pseudo code illustrates operation of accumulator 215:

```
// 40-bit Multi-Range Digital Accumulator circuit
module mrda (adc, range_select, clock_128 hz, por_n, accum_out);
output [39:0] accum_out;        // 40-bit output
reg    [39:0] accum_out;
input [7:0] adc;                // 8-bit ADC input
wire [7:0] adc;
input [1:0] range_select;       // 2-bit Range Select
wire [1:0] range_select;
input clock_128 hz,             // 128 Hz clock
    por_n;                      // active low Power-On Reset
wire clock_128 hz,
    por_n;
// internal nets
reg [39:0] latch_out;           // latch output
wire [22:0] multrng_out;        // multi-range selector output
// Hardware Definitions
// 40 bit adder - The MSB 17 bits of A input are zero
assign accum_out = {17'b00000000000000000, multrng_out[22:0]} +
latch_out[39:0];
// 40-bit latch
always @( negedge por_n or posedge clock_128 hz)
    if(!por_n)
      latch_out[39:0] <= 40'h0000000000;
    else
      latch_out[39:0] <= accum_out[39:0];
// multi-range selector
// when range_select is 11, adc is output on bits 22-15
// when range_select is 10, adc is output on bits 17-10
// when range_select is 01, adc is output on bits 12-5
//        otherwise, adc is output on bits 7-0
assign multrng_out[22:0] =
        (range_select[1:0] == 2'b11)?
            {adc[7:0], 15'b000000000000000}:
        (range_select[1:0] == 2'b10)?
            {5'b00000, adc[7:0], 10'b0000000000}:
        (range_select[1:0] == 2'b01)?
            {10'b0000000000, adc[7:0], 5'b00000}:
            {15'b000000000000000, adc[7:0]};
endmodule
```

In this embodiment of the present invention, accumulator 215 has a 40-bit capacity. This means that accumulator 215 is capable of accumulating 40 bits of digital data. However, if desired, the capacity of accumulator 215 can be increased. Increasing the number of bits in accumulator 215 will allow accumulator 215 to track battery usage for larger capacity batteries.

Referring, again, to FIGS. 2A and 2B, further description is provided concerning operation of battery charge indicator 160. Because accumulator 215 is clocked with clock signal 201, the accumulated bits of digital signals 213 correspond to current-time values of load current 202. In other words, each load current 202 has a "bit-weight" value measured in Ampere-Seconds (A-S).

The following formula (1) defines a bit-weight value for each bit in digital signal 213:

$$\text{Bit Weight}(A-S) = \frac{\text{Value of load current 202 bit weight}(A)}{\text{Value of clock signal 201(Hz)}} \quad (1)$$

where value of clock signal 201 is 128 Hz and value of load current 202 bit weight varies according to bit position. Table 7 illustrates bit-weight values according to formula (1) and bit positions in forty-bit output signal 217.

TABLE 7

Bit positions in the accumulator and corresponding bit-weight values

| Bit Position | Bit Weight (A-S) |
|---|---|
| 0 | 3.91 n |
| 1 | 7.81 n |
| 2 | 15.63 n |
| 3 | 31.3 n |
| 4 | 62.5 n |
| 5 | 125.0 n |
| 6 | 250.0 n |
| 7 | 0.5µ |
| 8 | 1.0µ |
| 9 | 2.0µ |
| 10 | 4.0µ |
| 11 | 8.0µ |
| 12 | 16.0µ |
| 13 | 32.0µ |
| 14 | 64.0µ |
| 15 | 128.0µ |
| 16 | 256.0µ |
| 17 | 512.0µ |
| 18 | 1.02 m |
| 19 | 2.05 m |
| 20 | 4.10 m |
| 21 | 8.19 m |

TABLE 7-continued

Bit positions in the accumulator and corresponding bit-weight values

| Bit Position | Bit Weight (A-S) |
|---|---|
| 22 | 16.38 m |
| 23 | 32.77 m |
| 24 | 65.54 m |
| 25 | 131.1 m |
| 26 | 262.1 m |
| 27 | 524.3 m |
| 28 | 1.05 |
| 29 | 2.10 |
| 30 | 4.19 |
| 31 | 8.39 |
| 32 | 16.78 |
| 33 | 33.55 |
| 34 | 67.11 |
| 35 | 134.22 |
| 36 | 268.44 |
| 37 | 536.87 |
| 38 | 1073.74 |
| 39 | 2147.48 |

As shown in Table 7, because accumulator 215 has a storage capacity of forty bits, there are forty bit positions (numbered 0 to 39). Each bit position corresponds to a particular current being drawn from battery 110. Based on Table 7, it can be seen that accumulator 215 has a capacity of about 4295 Amp-seconds.

Figure 3:
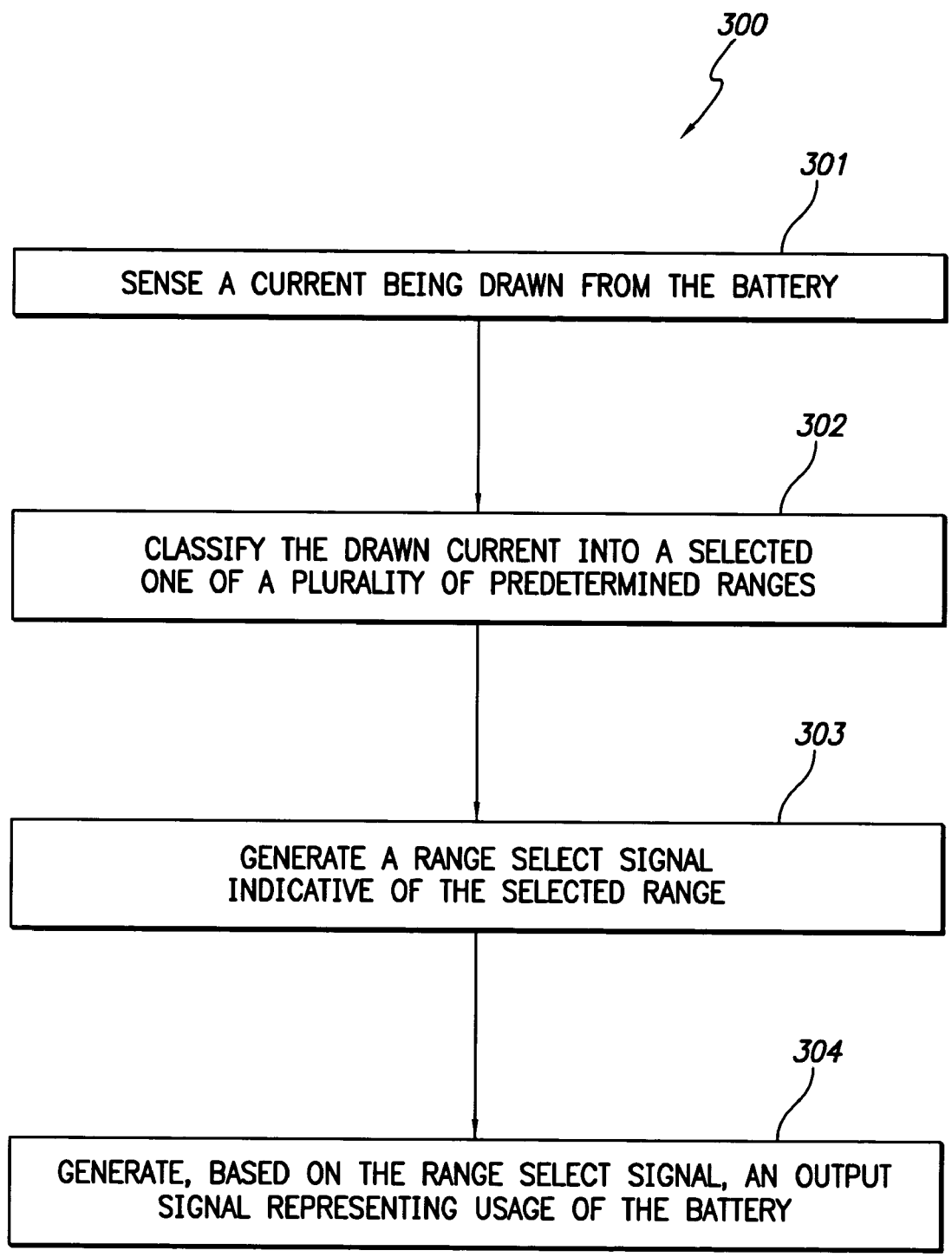
FIG. 3 is a flowchart illustrating a method for tracking battery usage in a cardiac device, according to the present invention.

FIG. 3 illustrates a method for tracking usage of battery 110 in an ICD 10, according to the present invention. In step 301, multirange current sensor 203 detects a current being drawn from battery 110. As described above, multirange current sensor 203 detects current being drawn from battery 110 and generates a voltage signal 209 indicative of the current being drawn.

In step 302, voltage signal 209 is amplified and digitized. Then, amplified and digitized voltage signal 209 is classified into one of four digital ranges corresponding to its respective current range. The processing then proceeds to step 303. In step 303, multirange current sensor 203 generates range select signals 221 and 222 indicative of the current range at which current is drawn. Range select signals 221 and 222 are used by accumulator 215 to determine the relative magnitude of the load current.

In step 304, accumulator 215 receives range select signals 221,222 and amplified and digitized voltage signal 209 (digital signal 213) from ADC 211. As described above, accumulator 215 assigns a bit position for the digital signal 213. Then, accumulator 215 accumulates bits of the digital signal 213 based on range select signals 221,222. Accumulator 215 then generates a 40-bit output signal 217 representing usage of battery 110, as shown in step 304.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A method for tracking battery usage in an implantable cardiac device, the method comprising:
routing current drawn from a battery through a current one of a plurality of selectable circuit configurations, each configuration corresponding to one of a plurality of ranges of current values;
measuring the voltage drop across the current circuit configuration;
generating a first signal based on the voltage drop, the first signal indicative of the load current being drawn from the battery;
for each first signal, generating a corresponding second signal indicative of the current range within which the load current falls;
switching to another of the plurality of selectable circuit configurations if the load current falls outside the range of the current circuit configuration;
repeating the measuring, generating and switching over time; and
determining usage of the battery by accumulating the load current over time as a function of corresponding first and second signals.

2. An apparatus for tracking battery usage in an implantable cardiac device, said apparatus comprising:
a component network coupled to receive current from the battery and have an associated voltage drop indicative of the current received from the battery, the network including a plurality of components and switches for arranging the components in one of a plurality of configurations, each configuration corresponding to a different range of current values;
an amplifier coupled to the component network and operative to output an amplified signal indicative of the current received from the battery;
a current range selector coupled to receive the amplified signal and operative to output a range select signal indicative of the range of current values within which the current received from the battery falls, and a control signal for setting the switches of the component network to form the component configuration corresponding to the range of current values indicated by the range select signal; and
an accumulator coupled to receive the amplified signal and the range select signal and operative to determine usage of the battery based on the amplified signal and the range select signal.

3. The apparatus of claim 2, wherein the ranges of current values comprise at least two ranges.

4. The apparatus of claim 3 wherein
a first current range is of up to about 128 μAmps;
a second current range is of up to about 4 mAmps;
a third current range is of up to about 128 mA; and
a fourth current range is of up to about 4 Amps.

5. The apparatus of claim 2, wherein the current range selector comprises:
a comparator for comparing a magnitude of the amplified signal to at least one reference voltage;
means for determining the range select signal based on the comparison.

6. The apparatus of claim 2, further comprising:
an analog to digital converter for receiving and digitizing the amplified signal prior to the amplified signal being provided to the accumulator.

7. The apparatus of claim 6, wherein the accumulator is a forty-bit multi-range digital accumulator.

8. The apparatus of claim 2 wherein the current range selector comprises:
  a comparator coupled to the amplifier to receive the amplified signal and compare the amplified signal to two reference voltages; and
  means for producing the range select signal based on the output of the comparator.

9. The apparatus of claim 8, wherein the means for producing the range select signal comprises:
  a counter coupled to the comparator and configured to count up or down based on the comparison by the comparator, the counter producing the range select signal.

10. The apparatus of claim 2 wherein the at least two ranges partially overlap.

11. The apparatus of claim 2 wherein the component network comprises a plurality of resistors that may be arranged in a plurality of different series configurations.

12. The apparatus of claim 2 wherein the current range selector comprises a decoder coupled to receive the range select signals and to output corresponding control signals as a function of the range select signals.

13. A circuit for tracking battery usage in an implantable cardiac device, said circuit comprising:

means for routing current drawn from a battery through a current one of a plurality of selectable circuit configurations, each configuration corresponding to one of a plurality of ranges of current values;

means for measuring the voltage drop across the current circuit configuration;

means for generating a first signal based on the voltage drop, wherein the first signal is indicative of the load current being drawn from the battery;

means for generating, for each first signal, a corresponding second signal indicative of the current range within which the load current falls;

means for switching to another of the plurality of selectable circuit configurations if the load current falls outside the range of the current circuit configuration; and means for determining usage of the battery by accumulating the load current over time as a function of corresponding first and second signals.

* * * * *